United States Patent [19]

Batz et al.

[11] Patent Number: 4,826,989
[45] Date of Patent: May 2, 1989

[54] PROCESS FOR THE PREPARATION OF LUCIFERIN COMPOUNDS

[75] Inventors: Hans-Georg Batz, Tutzing; Karl Wulff, Weilheim, both of Fed. Rep. of Germany

[73] Assignee: Boehringer Mannheim GmbH, Mannheim, Fed. Rep. of Germany

[21] Appl. No.: 95,122

[22] Filed: Sep. 10, 1987

Related U.S. Application Data

[63] Continuation of Ser. No. 495,222, May 19, 1983, abandoned, which is a continuation of Ser. No. 329,963, Dec. 11, 1981, abandoned, which is a continuation of Ser. No. 168,819, Jul. 10, 1980, abandoned.

Foreign Application Priority Data

Jul. 18, 1979 [DE] Fed. Rep. of Germany ........ 2929115

[51] Int. Cl.⁴ .............................................. C07D 417/04
[52] U.S. Cl. ..................................................... 548/169
[58] Field of Search ......................................... 548/169

[56] References Cited

PUBLICATIONS

Fusor, *Advanced Organic Chemistry*, 178–81 (Wiley, 1950).
White et al., "Analogs of Firefly Luciferin", J. Org. Chem. 30, 2344–8 (1965).
Ho et al., "Spaltung von Esters und Ethers mit Iodotrimethylsilan", Argu. Chemie 15, 847 (1976).
Starks, "Phase-Transfer Catalysis. I. Heterogeneous Reactions, . . . ", J.A.C.S. 93, 195–9 (1971).

*Primary Examiner*—David B. Springer
*Attorney, Agent, or Firm*—Felfe & Lynch

[57] ABSTRACT

The present invention provides a process for the preparation of compounds of the general formula:

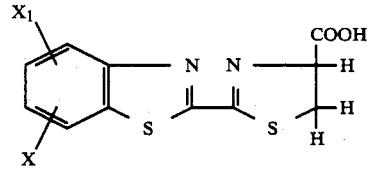

in which X is a hydroxyl group and $X_1$ is a hydrogen atom or a hydroxyl group, and especially of luciferin, by the reaction of D-cysteine with 2-cyanomono- or -dihydroxybenzothiazole obtained from 2-chloromono- or -dimethoxybenzothiazole via a demethylation, wherein the demethylation is accomplished by reaction with iodotrimethylsilane or with a mixture of phenyltrimethylsilane and iodine and hydrolysis under mild conditions of the silyl derivative formed.

21 Claims, No Drawings

PROCESS FOR THE PREPARATION OF LUCIFERIN COMPOUNDS

This is a continuation of application Ser. No. 495,222 filed on May 19, 1983, abandoned which is a continuation of application Ser. No. 329,963 filed on Dec. 11, 1981, now abandoned. Applicaton Ser. No. 329,963 was a continuation of application Ser. No. 168,819 filed on July 10, 1980, now abandoned.

The present invention is concerned with a process for the preparation of luciferin and of related compounds.

D-Luciferin, which has the structural formula:

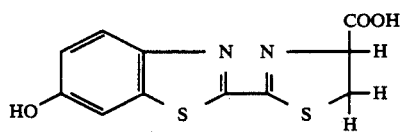

is the substrate for the enzyme luciferase. In recent times, luciferin has become of increasing interest since it is used as a vary sensitive detection reagent in clinical-chemical analysis.

Since the isolation of luciferin, which chemically is D-(-)-2-(6'-hydroxy-2'-benzothiazolyl)-$\Delta^2$-thiazoline-4-carboxylic acid and which is the substrate responsible for the luminescent reaction of the firefly, is very expensive to obtain from natural sources, very soon after its structure had been elucidated, attempts were made to synthesize it (see White et al., J.A.C.S., 83, 2402/1961).

The last two stages of the synthesis of White et al., i.e. an ester splitting for converting 2-cyano-6-methoxybenzothiazole into 2-cyano-6-hydroxybenzothiazole and the reaction of this latter compound with D-cysteine, is to be found again in all previously described synthesis (see also L. J. Bowie, Methods in Enzymology, Vol. LVII, 15/1978).

The only variations which have previously been made were in the synthetic route to the key compound of the synthesis, i.e. 2-cyano-6-methoxybenzothiazole (see Whiite et al., J. org. Chem., 30, 2344/1965). Starting from commercially available 2-amino-6-methoxybenzothiazole, this process proceeds via a diazotization and a Sandmeyer reaction to give 2-chloro-6-methoxybenzothiazole. The most critical stage of the whole synthesis, namely, the ether splitting, takes place according to this process and also according to the other known synthesis with pyridine hydrochloride. However, even with this admittedly very mild reagent, it is only possible to obtain yields of the ether splitting of 15 to 30%.

Recently, a new method of carrying out ether splitting has been reported (Ho and Olah, Angew. Chemie, International Edition, 15, 774/1976) in which the splitting reagent used is iodotrimethylsilane or a mixture of phenyltrimethylsilane and iodine. However, the use of this ether splitting method is only described for simple ethers in which no other reactive groups are present in the molecule.

Since luciferin is very difficult to purify, as has already been ascertained by White et al. (J.A.C.S., 83, 2402/1961), it is an object of the present invention to provide a process for the preparation of luciferin with which it is possible to obtain this compound in high yields and in a very high state of purity so that laborious purification processes, such as the previously used chromatography, are no longer necessary.

Surprisingly, we have now found that the ether splitting method described by Ho and Olah can be applied to the not very stable and multifunctional 2-chloro-6-methoxybenzothiazole and that this is possible with substantially better yields and with the achievement of substantially purer products than was possible with the previously known processes. This was not to have been expected since, having regard to the known analogy between oxygen ethers and thioethers, a fission of the thiazole ring was to have been expected. However, surprisingly, this fission does not occur, even though the reaction takes place on the nitrogen atom. This process is equally suitable for analogous compounds with one or two methoxy radicals in the benzene ring.

Thus, according to the present invention, there is provided a process for the preparation of compounds of the general formula:

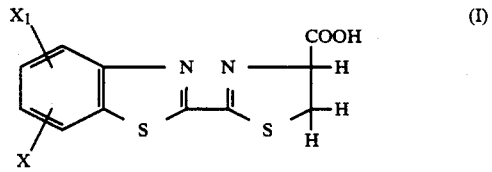

wherein X is a hydroxyl group and $X_1$ is a hydrogen atom or a hydroxyl group, and especially of luciferin, by the reaction of D-cysteine with 2-cyanomono- or -dihydroxybenzothiazole prepared from 2-chloromono- or -dimethoxybenzothiazole via a demethylation, wherein the demethylation is carried out by reaction with iodotrimethylsilane or with a mixture of phenyltrimethylsilane and iodine and hydrolysis under mild conditions of the silyl derivative formed.

The reaction with iodotrimethylsilane or with a mixture of phenyltrimethylsilane and iodine is preferably carried out with the exclusion of moisture at a temperature of from ambient temperature to about 150° C. and preferably at a temperature of from about 70° to about 110° C. This reaction is advantageously carried out in an organic solvent which is inert under the reaction conditions at a temperature of up to the reflux temperature of the solvent. Preferred examples of solvents which can be used include chloroform, methylene chloride, carbon tetrachloride and/or tetramethylenesulphone.

In carrying out the reaction, per mold equivalent of methyl radical to be split off, there are used at least 2 moles of iodotrimethylsilane or of the phenyltrimethylsilane/iodine mixture. When using a mixture of phenyltrimethylsilane/iodine, it is preferable to use a mixture which contains 2 gram atoms of iodine per mole of phenyltrimethylsilane.

The hydrolysis of the silyl derivative formed by the reaction with iodotrimethylsilane or with the mixture of phenyltrimethylsilane and iodine is preferably carried out by first treating with an aliphatic alcohol containing up to 4 carbon atoms, preferably methanol, and then with a complexing agent for the iodine liberated by the reaction. The preferred complexing agent used is sodium thiosulphate, it being preferable to use a 1 to 20% by weight and more preferably a 5 to 10% by weight aqueous solution of sodium thiosulphate.

By means of the use of this mild hydrolysis, which is preferably carried out at ambient temperature, a side reaction with methanol can be almost completely supressed so that the desired end product are obtained with a high degree of purity.

The process according to the present invention can be advantageously carried out with different sequences of the reaction steps, namely, the formation of the silyl derivative and the introduction of the cyano group into the 2-position. These various reaction possibilities can be seen from the following reaction scheme, using luciferin as an example:

Finally, the process according to the present invention can also be carried out by reacting 2-chloromono- or -dimethoxybenzothiazole with an alkali metal cyanide, preferably with potassium cyanide, reacting the 2-cyanomono- or -dimethoxybenzothiazole (IV) formed with iodotrimethylsilane and hydrolyzing the product obtained, preferably with methanol and an aqueous solution of sodium thiosulphate.

In the case of these preferred embodiments of the process according to the present invention, the reaction

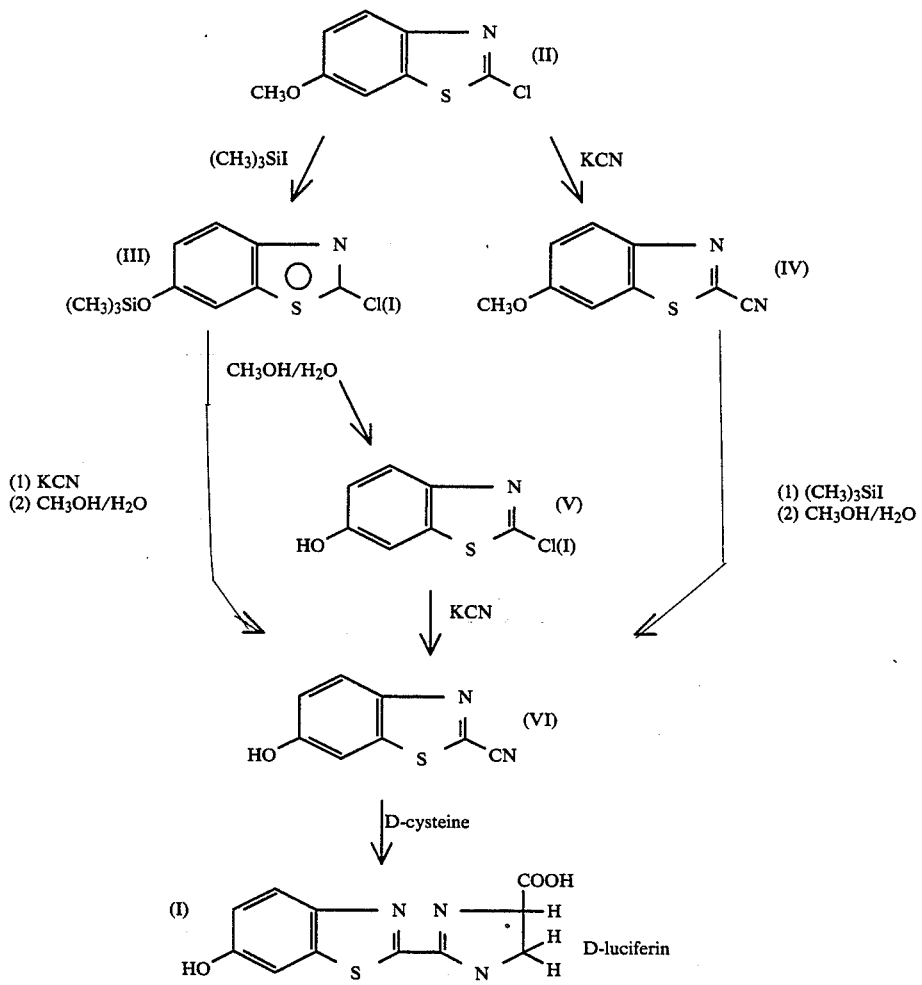

According to one preferred embodiment of the process according to the present invention, 2-chloromono- or -dimethoxybenzothiazole (II) is first reacted with iodotrimethylsilane and the product obtained then hydrolysed, preferably by treatment with methanol and an aqueous solution of sodium thiosulphate, whereupon the mixture formed of 2-chloromono- or -dihydroxybenzothiazole and 2-iodomono- or -dihydroxybenzothiazole (V) is reacted with an alkali metal cyanide and preferably with potassium cyanide.

According to another preferred embodiment of the process according to the present invention, 2-chloromono- or -dimethoxybenzothiazole is first reacted with iodotrimethylsilane and the product obtained reacted with an alkali metal cyanide and preferably with potassium cyanide before hydrolyzing the product obtained, which is preferably carried out with methanol in an aqueous solution of sodium thiosulphate.

with the alkali metal cyanide is preferably carried out in an inert organic solvent and especially in dimethyl sulphoxide, in the presence of a phase transfer catalyst. The phase transfer catalyst thereby used can be a quaternary alkylammonium salt and preferably a tetralkylammonium salt, the alkyl radicals of which contain up to 4 carbon atoms, for example tetrabutylammonium bromide, or can be a crown ether, especially 18-crown-6. Catalysis with the help of a phase transfer catalyst has proved to be especially effective for the methoxy compound. This catalysis is also of advantage in the case of the reaction of the N-trimethylsilylmono- or -dimethylsilyloxybenzothiazole formed as intermediate since, in this way, it is possible to combine both steps.

Surprisingly, we have found that in the case of the process according to the present invention, the hydroxy-2-cyanobenzothiazole formed is obtained in a purer form with the simple reaction sequence employed than in the case of any of the other previously known syntheses. Consequently, laborious purification procedures, such as a chromatographic purification, are no longer necessary and the final coupling with D-cysteine leads to very pure D-luciferin or analogues thereof.

Furthermore, it has proved to be especially advantageous to purify the product by suspending it in water which has been gassed with nitrogen, mixing the suspension with sodium bicarbonate, extracting the solution obtained with an inert organic solvent, for example ethyl acetate, acidifying the aqueous phase, for example with hydrochloric acid, and leaving to stand for crystallization. In this manner, a chromatographically pure product is obtained.

The following Examples are given for the purpose of illustrating the present invention:

EXAMPLE 1

2-Chloro-6-methoxybenzothiazole

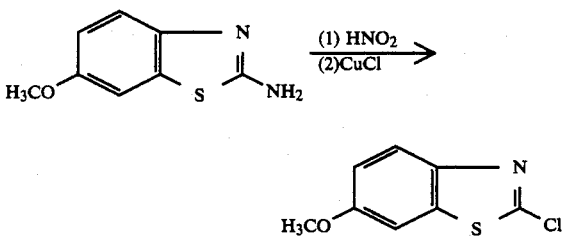

54 g. (0.3 mol) 2-Amino-6-methoxybenzothiazole are dissolved in 150 ml. formic acid, 60 ml. glacial acetic acid and 120 ml. concentrated hyrochloric acid. While stirring, there is then added dropwise at −5° C., a solution of 21 g. sodium nitrite in 30 ml. water. The redbrown solution obtained is stirred for 15 minutes at 0° C. Subsequently, the solution is introduced portionwise at 0° C. into a vigorously stirred solution of 39 g. (0.39 mol) cuprous chloride in 180 ml. 28% hydrochloric acid, a vigorous evolution of gas being observed. Subsequently, the reaction mixture is allowed to warm up to ambient temperature and then stirred overnight at this temperature. The solution is then poured into about 1 liter of ice water and the precipitated product is filtered off with suction and washed with water.

The moist product is taken up in about 800 ml. methanol, stirred and separated off from undissolved material. The filtrate is mixed with charcoal, filtered and the organic solvent stripped off in a vacuum at 50° C. The suspension remaining behind is diluted with water and filtered off with suction. The moist product is dissolved in about 600 ml. ethyl acetate, a small amount of undissolved material remaining behind, and the solution is dried with anhydrous sodium sulphate. Charcoal is added thereto, followed by suction filtration. The filtrate is evaporated to dryness in a vacuum and the residue is dried in a desiccator.

There are obtained 32.75 g. 2-chloro-6-methoxybenzothiazole, which corresponds to a yield of 54.6% of theory (according to the literature, a yield of only 35 to 45% of theory is obtained).

The product obtained has a melting point of 48° to 49° C. and is chromatographically pure.

EXAMPLE 2

2-Chloro-6-hydroxybenzothiazole

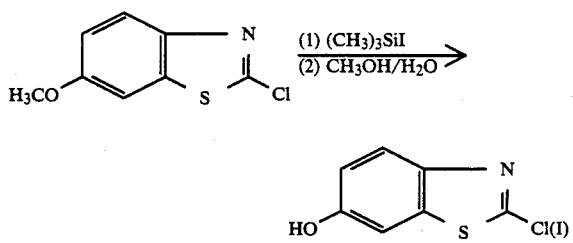

10 g. (0.05 mol) of 2-chloro-6-methoxybenzothiazole prepared according to Example 1 are dissolved in 30 ml. anhydrous chloroform. 21 g. (about 0.1 mol; 15 ml.) iodotrimethylsilane and then added thereto and the reaction mixture stirred under reflux at a bath temperature of 80° C., with the exclusion of moisture. After a reaction time of 70 hours, a further 4 ml. iodotrimethylsilane are added thereto and stirring continued for a further 40 hours at reflux temperature.

Subsequently, the reaction solution is suspended in about 400 ml. chloroform and 100 ml. methanol are added thereto, followed by brief shaking, a clear solution thereby being obtained. 300 ml. of a 10% aqueous solution of sodium thiosulphate are immediately added thereto, followed by shaking. The chloroform phase is separated off and the aqueous phase is extracted twice with chloroform. The combined extracts are dried with anhydrous sodium sulphate, mixed with charcoal, filtered and evaporated in a vacuum.

There are obtained 8.4 g. of a crude product which is suspended in 300 ml. water, mixed with 20 ml. aqueous 2N sodium hydroxide solution and shaken. After a short time, a small amount of an insoluble product is filtered off with suction and washed with water. The turbid filtrate is mixed with charcoal and filtered off with suction, whereupon the filtrate is acidified with 2N hydrochloric acid. The precipitated product is then filtered off with suction, washed with water and dried in a desiccator.

There are obtained 6.28 g. of a mixture of 2-chloro-6-hydroxybenzothiazole and 2-iodo-6-hydroxybenzothiazole, which corresponds to a yield of 67.6% of theory (according to the process described in the literature, this compound is obtained in a yield of only 15 to 32%). The product melts at 160°–164° C., is chromatographically pure and corresponds to the statements given in the literature.

EXAMPLE 3

2-Cyano-6-hydroxybenzothiazole

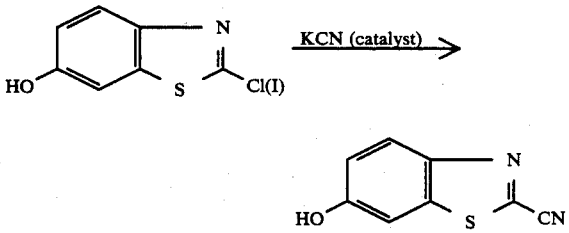

4 g. of the mixture of 2-chloro-6-hyroxybenzothiazole and 2-iodo-6-hydroxybenzothiazole obtained in Example 2 are added to a suspension of 3 g. potassium cyanide and 100 mg. 18-crown-6 in 150 ml. dimethyl sulphoxide heated to 120° C. and stirred at a bath temperature of 120° C. After a reaction time of 3 hours, the reaction mixture is poured in 1 liter of ice water and the solution obtained is acidified with dilute hydrochloric acid. Subsequently, it is extracted twice with 500 ml. amounts of diethyl ether and the extracts are washed with water, dried over anhydrous sodium sulphate, mixed with charcoal, filtered and the filtrate evaporated in a vacuum. 2.5 g. Crude 2-cyano-6-hydroxybenzothiazole are obtained.

The crude product is suspended in 100 ml. water and mixed with a 1N aqueous sodium hydroxide solution, the material thereby dissolving in a short time with a little insoluble material remaining behind. Charcoal is added thereto, followed by suction filtration. The filtrate is acidified with dilute hydrochloric acid and the precipitated crystals are filtered off with suction and dried in a desiccator. The product is dissolved in 150 ml. diethyl ether, washed with 100 ml. ligroin to precipitate impurities, mixed with charcoal and filtered with suction. The filtrate is evaporated in a vacuum to give 2.0 g. 2-cyano-6-hydroxybenzothiazole. The compound melts, with decomposition, at 190°–200° C.

EXAMPLE 4

D-Luciferin

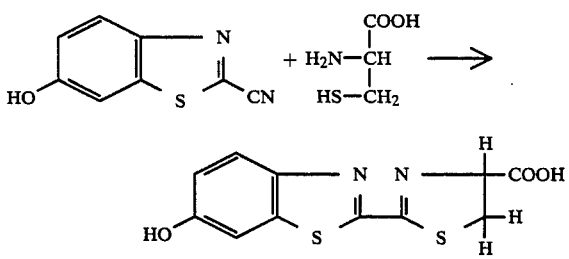

685 mg. (3.9 mMol) D-cysteine hydrochloride monohydrate are dissolved in 13 ml. water which has been previously gassed with nitrogen. A pH value of 8 is adjusted, under an atmosphere of nitrogen, with about 6 ml. of a 1N aqueous sodium hydroxide solution and then a solution of 528 mg. (3 mMol) 2-cyano-6-hydroxybenzothiazole in 22 ml. methanol (analytically pure) is added thereto under an atmosphere of nitrogen. The yellow solution is stirred under an atmosphere of nitrogen and with the exclusion of light for 1 hour at ambient temperature. Subsequently, the solution is acidified with 3 ml. of 2N hydrochloric acid and left to stand for about 3 hours at 4° C. The precipitated crystals are filtered off with suction under an atmosphere of nitrogen, washed with methanol and water (1:1 v/v) and dried in a desiccator with the exclusion of light. 0.75 g. D-Luciferin are obtained, which corresponds to a yield of 89.3% of theory. The compound melts at 187°–188° C., with decomposition, and is chromatographically identical with the product known from the literature but contains small amounts of impurities.

150 mg. of this crude product are suspended in 8 ml. water which has been gassed with nitrogen and mixed with sodium bicarbonate. After a short time, a solution is obtained. This solution is immediately extracted with ethyl acetate, the organic phase is separated off and the aqueous phase is acidified with 2N hydrochloric acid. After standing for 1 hour at 4° C., the crystals are filtered off with suction and dried in a desiccator. There is obtained 0.1 g. of chromatographically pure D-luciferin which behaves as a substrate for luciferase in a manner identical to the product known from the literature.

EXAMPLE 5

2-Cyano-6-hydroxybenzothiazole

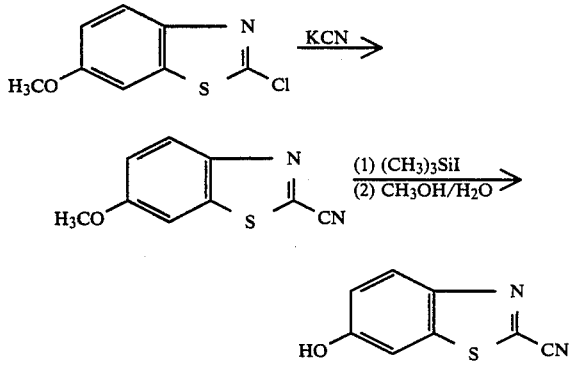

4 g. (0.02 mol) 2-Chloro-6-methoxybenzothiazole and 2.6 g. (0.04 mol) potassium cyanide are stirred in 150 ml. dimethyl sulphoxide for 3 hours at 100° C. The solution is then cooled and poured into about 1 liter of water and extracted twice with diethyl ether. The ethereal extracts are washed with water, dried with anhydrous sodium sulphate and evaporated.

The evaporation residue is dissolved in 5 ml. chloroform, mixed with 6 ml. iodotrimethylsilane and stirred for about 100 hours at a bath temperature of 85° C. The solution is then diluted with chloroform and some methanol is added thereto, followed by brief shaking. Subsequently, the solution is skaken with a 5% solution of sodium thiosulphate, the organic phase is separated off and the aqueous phase is extracted with chloroform. The combined chloroform extracts are dried with anhydrous sodium sulphate and evaporated. The crude product thus obtained is purified over a column packed with silica gel, using tetrahydrofuran/diisopropyl ether (1:4 v/v) as elution agent. 1.5 g. 2-Cyano-6-hydroxybenzothiazole are obtained which corresponds to a yield of 45% of theory. The compound melts, with decomposition, at 190°–200° C.

From the above Examples, it can be readily seen that the process according to the present invention leads, with considerably better yields, to a substantially purer product, namely D-luciferin, and thus represents a considerable enrichment of the technology.

EXAMPLE 6

2-Cyano-6-hydroxybenzothiazole (Variant 3)

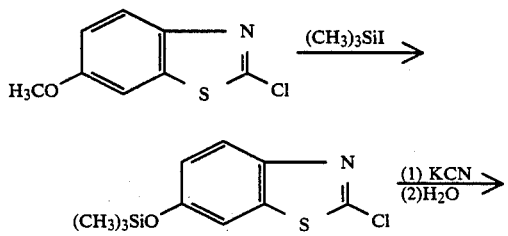

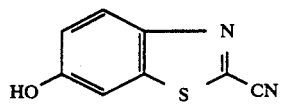

3 g. (0.015 mol) 2-Chloro-6-methoxybenzothiazole are dissolved in 9 ml. anhydrous chloroform and mixed with 6 g. (4.5 ml.) (0.03 mol) iodotrimethylsilane. The solution is stirred under reflux at a bath temperature of 80° C.

After 25 hours, a further 3 g. (2.1 ml.) iodotrimethylsilane are added thereto and the reaction mixture stirred under reflux. After a further reaction period of 30 hours, the solution is evaporated in a vacuum. The residue is dissolved in 100 ml. dimethyl sulphoxide and mixed with 3 g. potassium cyanide (the three fold molar amount). The suspension is then stirred at 100° C.

After a reaction period of 3 hours, the reaction mixture is poured into about 800 ml. ice-water, acidified with 2N hydrochloric acid, extracted once with 500 ml. and once with 300 ml. of diethyl ether. The combined extracts are washed with water, dried with anhydrous sodium sulphate and evaporated. The still slightly contaminated product is purified over silica gel 60 with diisopropyl ether-tetrahydrofuran (4:1 v/v). The yield is 42% of theory.

EXAMPLE 7

The process according to Examples 1 to 4 is repeated but, instead of 2-amino-6-methoxybenzothiazole, there is used an equivalent amount of 2-amino-4,6-dimethoxybenzothiazole. The amount of iodotrimethylsilane used is 0.15 mol. In this manner, 4'-hydroxyluciferin is obtained.

It will be understood that the specification and examples are illustrative but not limitative of the present invention and that other embodiments within the spirit and scope of the invention will suggest themselves to those skilled in the art.

What is claimed is:

1. In a process for the preparation of a luciferin compound of the formula

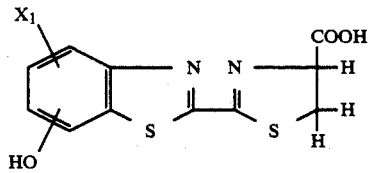

wherein $X_1$ is hydrogen or hydroxyl, the improvement comprising reacting D-cysteine with 2-cyanomono- or 2-cyanodi-hydroxybenzothiazole obtained from 2-chloromono- or 2-chlorodi-methoxybenzothiazole via a demethylation with iodotrimethylsilane or with a mixture of phenyl trimethylsilane and iodine to obtain a silyl derivative, and thereafter hydrolyzing said silyl derivative with an alkanol containing up to 4 carbon atoms, thereby obtaining a chromatographically pure luciferin compound.

2. Process as claimed in claim 1 wherein the reaction is carried out under the exclusion of moisture at room temperature to about 150° C.

3. Process as claimed in claim 1 wherein the reaction is carried out in an inert organic solvent at a temperature ranging from room temperature to the reflux temperature of the solvent.

4. Process as claimed in claim 3 wherein the solvent used is at least one of chloroform, methylene chloride, carbon tetrachloride and tetramethylenesulphone.

5. Process as claimed in claim 1 wherein per mole equivalent of methyl radicals to be split off, there are used at least 2 moles of iodotrimethylsilane.

6. Process as claimed in claim 1 wherein per mole equivalent of methyl radicals to be split off, there are used at least 2 moles of the phenyl trimethylsilane/iodine mixture.

7. Process as claimed in claim 1 wherein the alkanol used is methanol.

8. Process as claimed in claim 1 further comprising adding sodium thiosulphate as a complexing agent for iodine liberated in the hydrolysis reaction.

9. Process as claimed in claim 1 wherein the hydrolysis is carried out at room temperature.

10. In a process for the production of a luciferin compound of the formula

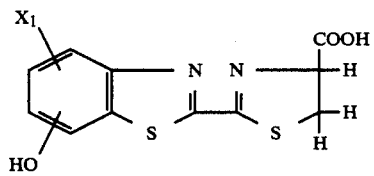

wherein $X_1$ is hydrogen or hydroxyl, the improvement comprising the steps of:
(a) reacting 2-chloromono- or 2-chlorodi-methoxybenzothiazole with iodotrimethylsilane; thereafter
(b) hydrolyzing the silyl derivative formed in (a) by reacting said derivative with methanol and an aqueous solution of potassium cyanide to form a reaction mixture; thereafter
(c) reacting the reaction mixture of (b) with an alkali metal cyanide; and thereafter
(d) reacting the reaction mixture of (c) with D-cysteine, whereby a chromatographically pure luciferin compound is obtained.

11. Process as claimed in claim 10 wherein the reaction with the alkali metal cyanide is carried out in an inert organic solvent and in the presence of a phase-transfer catalyst selected from the group consisting of tetraalkylammonium salts and crown ethers.

12. Process as claimed in claim 11 wherein the inert organic solvent is dimethyl sulphoxide.

13. Process as claimed in claim 11 wherein the phase transfer catalyst is a crown ether.

14. Process as claimed in claim 13 wherein the crown ether is 18-crown-6.

15. Process as claimed in claim 10 wherein the alkali metal cyanide used is potassium cyanide.

16. Process as claimed in claim 1 for the preparation of luciferin.

17. Process as claimed in claim 16 wherein the luciferin obtained is suspended in water which has been gassed with nitrogen and mixed with sodium bicarbonate, and the solution obtained is extracted with an inert organic solvent, and the aqueous phase is acidified and left to stand to crystallize out luciferin.

18. Process as claimed in claim 17 wherein the inert organic solvent used is ethyl acetate.

19. Process as claimed in claim 1 wherein the starting material used is 2-chloro-6-methoxybenzothiazole or 2-chloro-4,6-dimethoxybenzothiazole.

20. In a process for the production of a luciferin compound of the formula

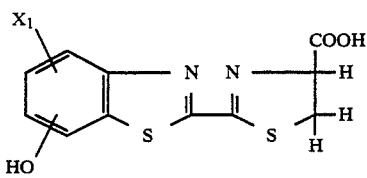

wherein $X_1$ is hydrogen or hydroxyl, the improvement comprising the steps of:
  (a) reacting 2-chloromono- or 2-chlorodimethoxybenzothiazole with iodotrimethylsilane; thereafter
  (b) reacting the silyl derivative formed in (a) with an alkali metal cyanide to form a reaction mixture; thereafter
  (c) hydrolyzing reaction mixture (b) with methanol and an aqueous solution of potassium cyanide; and thereafter
  (d) reacting the reaction mixture (c) with D-cysteine, whereby a chromatographically pure luciferin compound is obtained.

21. In a process for the production of a luciferin compound of the formula

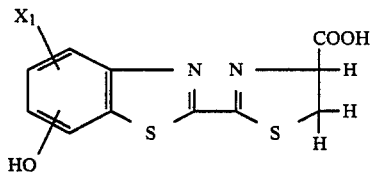

wherein $X_1$ is hydrogen or hydroxyl, the improvement comprising the steps of:
  (a) reacting 2-chloromono or 2-chlorodi-methoxybenzothiazole with an alkali metal cyanide; thereafter
  (b) reacting the reaction mixture (a) with iodotrimethylsilane; thereafter
  (c) hydrolyzing the reaction mixture (b) with methanol and an aqueous solution of potassium cyanide; and thereafter
  (d) reacting the reaction mixture (c) with D-cysteine, whereby a chromatographically pure luciferin compound is obtained.

* * * * *

UNITED STATES PATENT AND TRADEMARK OFFICE
CERTIFICATE OF CORRECTION

PATENT NO. : 4,826,989
DATED : May 2, 1989
INVENTOR(S) : Hans-Georg Batz et al.

It is certified that error appears in the above-identified patent and that said Letters Patent is hereby corrected as shown below:

Column 1, line 24: change "vary" to -- very --.

Column 3, formula (III) should read as follows:

(III)

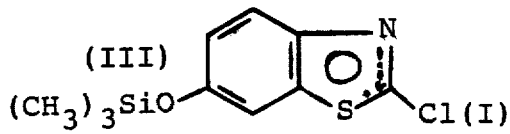

Column 3, formula (I) should read as follows:

(I)

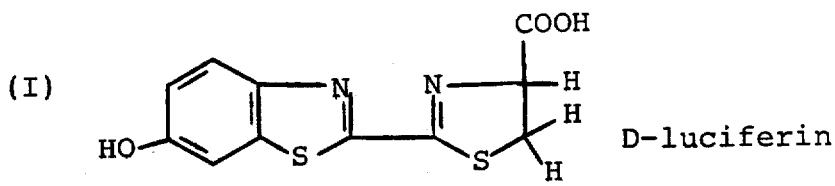

D-luciferin

Column 4, line 62: change "dimethylsilyloxybenzothiazole" to read -- ditrimethylsilyloxybenzothiazole --.

Signed and Sealed this

Twenty-fourth Day of April, 1990

Attest:

HARRY F. MANBECK, JR.

Attesting Officer     Commissioner of Patents and Trademarks